US007955829B2

(12) United States Patent
Caussette et al.

(10) Patent No.: US 7,955,829 B2
(45) Date of Patent: Jun. 7, 2011

(54) METHOD FOR THE INACTIVATION OF AMYLASE IN THE PRESENCE OF PROTEASE

(75) Inventors: Mylene Caussette, Lille (FR); Frederik Miggelbrink, Lille (FR); Gregory Maufroid, Baisieux (FR)

(73) Assignee: DSM IP Assets B.V., Heerlen (NL)

( * ) Notice: Subject to any disclaimer, the term of this patent is extended or adjusted under 35 U.S.C. 154(b) by 1209 days.

(21) Appl. No.: 10/499,663

(22) PCT Filed: Dec. 18, 2002

(86) PCT No.: PCT/EP02/14529
§ 371 (c)(1),
(2), (4) Date: Nov. 16, 2004

(87) PCT Pub. No.: WO03/052092
PCT Pub. Date: Jun. 26, 2003

(65) Prior Publication Data
US 2005/0064573 A1    Mar. 24, 2005

(30) Foreign Application Priority Data
Dec. 19, 2001   (EP) .................................. 01204991

(51) Int. Cl.
*C12N 9/99* (2006.01)
(52) U.S. Cl. ...................................... 435/184
(58) Field of Classification Search .................. 435/183, 435/189, 190, 191
See application file for complete search history.

(56) References Cited

U.S. PATENT DOCUMENTS

| 2,683,682 A * | 7/1954 | Miller et al. ................... 435/184 |
| 3,988,207 A | 10/1976 | Aunstrup ....................... 435/223 |
| 4,086,139 A * | 4/1978 | Hoerle .......................... 435/184 |
| 4,357,357 A * | 11/1982 | Branner-Jorgensen et al. 426/36 |
| 4,591,565 A | 5/1986 | Branner-Jorgensen et al. ............. 435/223 |
| 4,943,530 A | 7/1990 | Christner et al. ............. 435/188 |
| 5,139,943 A | 8/1992 | Heinsohn et al. ............. 435/226 |
| 5,800,849 A * | 9/1998 | Budtz et al. ..................... 426/36 |
| 2002/0160445 A1* | 10/2002 | Harboe ........................ 435/69.1 |

FOREIGN PATENT DOCUMENTS

| EP | 0238023 | 10/2002 |
| EP | 0700253 | 5/2003 |
| GB | 2038339 | 7/1980 |
| GB | 2045772 | 11/1980 |
| GB | 2045773 | 11/1980 |
| WO | WO 97/20921 | 6/1997 |

OTHER PUBLICATIONS

Yada R. Y., and Nakai, S., J Agric. Food Chem 1986, 34, 675-679.*
International Search Report for PCT/EP02/14529, mailed on Aug. 1, 2003, 4 pages.
Sternberg, J. Dairy Sci. (1971) 2(54):159-167.

* cited by examiner

*Primary Examiner* — Kade Ariani
(74) *Attorney, Agent, or Firm* — Nixon & Vanderhye P.C.

(57) ABSTRACT

The invention relates to a method for the inactivation of amylase in a solution comprising *Rhizomucor miehei* aspartic protease by keeping the solution at a pH between 2.1 and 2.8 and at a temperature between 20° C. and 40° C. for a period of time sufficient to inactivate amylase for at least 95%. With this method the level of residual *Rhizomucor miehei* aspartic protease activity in the solution at the end of the heating time is at least 90%, preferably at least 95%, and the residual amylase activity is 0.05 RAU/g or lower, more preferably 0.001 RAU/g or lower, i.e. more than 99% of the amylase activity has been inactivated.

38 Claims, No Drawings

METHOD FOR THE INACTIVATION OF AMYLASE IN THE PRESENCE OF PROTEASE

CROSS-REFERENCE TO RELATED APPLICATIONS

This application is the national stage of PCT application PCT/EP02/14529 having an international filing date of 18 Dec. 2002, which claims priority from European application 01204991.2, filed 19 Dec. 2001. The contents of these documents are incorporated herein by reference.

This invention relates to a method for the inactivation of amylase in the presence of protease. The invention further relates to a *Rhizomucor miehei* aspartic protease obtainable by the method of the invention and to its use in the making of dairy products.

Chymosin, extracted from the calf stomach is, at present, one of the most efficient milk-clotting enzymes known and is largely used in the production of cheese. However the increasing demand for chymosin by the dairy farming industry and its limited availability from natural sources has prompted scientists to search for suitable alternatives. Chymosin can now be produced via recombinant DNA technology in bacteria, i.e. *Escherichia coli*, yeast, i.e. *Kluyveromyces lactis*, and in filamentous fungi, i.e. *Aspergillus niger*. Also fungal proteases are now being extensively used in cheese production. *Rhizomucor miehei* aspartic protease is the most common; milk-clotting preparation for its good performance (Sternberg, M. Z. (1971) Crystalline milk clotting protease from *Mucor miehei*, and some of its properties. *J. Dairy Sci.*, Vol. 54, page 159-167). This protease can also be produced heterologously via recombinant DNA technology in filamentous fungi (Boel E. et al. European Patent EP-238023). *Rhizomucor miehei* aspartic protease is highly heat stable. It remains partially active in the whey after pasteurisation, causing undesired milk clotting when the whey is used in other preparations, like in enriched milk for baby food. Therefore, *Rhizomucor miehei* aspartic protease is often modified to decrease its heat stability. Several methods to increase thermal destabilisation of *Rhizomucor miehei* aspartic protease are known in the art. Some of them are described in the UK Patents GB 2038339B, GB 2045772B and GB 2045773B.

A problem with the microbial production of milk-clotting enzymes via fermentation is the expression of other undesirable enzymes. Because of an increasing demand in the market for pure enzyme preparations, several methods have been developed in the art for the separation and purification of desirable enzymes from enzyme mixtures or for the selective inactivation of undesirable enzymes.

U.S. Pat. No. 2,683,682 (1954) discloses the differential inactivation of one of the enzymes of the group consisting of proteases and amylases from mixtures comprising both enzyme types. The method comprises adjusting the pH of the aqueous solution between 3.0 and 4.5 (to selectively inactivate amylase) or between 7.0 and 10.5 (to selectively inactivate protease) and maintaining the mixture at a temperature comprised between about 5° C. and 60° C. for a period of time sufficient to inactivate the undesired enzyme, generally from about 0.5 hours or lower for higher temperatures, to 20 hours for lower temperatures. Treatment of enzyme mixtures derived from malted wheat flour or malted barley at pH 3.6 and 50° C. for 0.5 hours leads to a protease recovery of at best 66% and amylase deactivation of 99.7%. At the same pH and 5° C. for 20 hours the protease recovery is 85%, with an amylase deactivation of 99.6%.

U.S. Pat. No. 4,086,139 (1978) describes the selective inactivation of amylase in enzyme mixtures comprising protease and amylase. The inactivation of amylase occurs by treating the enzyme mixture with an oxidising agent selected from the group consisting of chlorite and hypochlorite ions. The ions are added to the enzyme mixture in sufficient amount to inactivate the amylase while leaving the protease intact, thus avoiding further purification steps. Temperature and pH of the treatment are not critical as far as they are not detrimental to the protease. The enzyme compositions, which can be treated with the method of the invention, are derived from animal organs (e.g. crude animal organ extracts) or bacteria like *Bacillus subtilis* or *licheniformis* (e.g. fermentation broths). With the method of the invention more than 80% of the amylase is inactivated leaving the protease activity more than 80% intact.

U.S. Pat. No. 5,139,943 (1992) describes a method for selective recovery of microbially produced chymosin from mixtures of polypeptides or enzymes produced by fermentation, like for example α-amylase. The method of the invention is based on the use of a two phase, liquid-liquid system having partition coefficient for chymosin greater than about 85. The two-phase system is obtained by adding PEG and a salt like a phosphate or a sulphate to the aqueous enzyme composition. The chymosin is selectively extracted into the organic phase while the amylase stays in the water phase. Chymosin can be recovered from the PEG via ion exchange chromatography. By using a pH lower than 3, partition coefficients for chymosin can be obtained of about 1000, allowing full separation from amylase and a chymosin recovery of about 96-98%.

International Patent Application WO 97/20921 (published Jun. 12, 1997) describes a method for the selective inactivation of at least one undesirable enzyme from an enzyme mixture comprising desirable and undesirable enzymes. The enzyme mixture is treated at pH lower than 5 and at a temperature from 2 to 75° C. for at least 20 seconds, and/or at pH higher than 9 and at a temperature from 2 to 75° C. for at least 20 seconds. By this method amylase is completely inactivated by treating an enzyme mixture comprising amylase and cellulase at pH 3.5 for 1 min at 70° C., while 96% of the cellulase activity remains intact (Example 4). On the other hand only 2% of the protease activity is left when treating an enzyme mixture comprising lipase and protease at pH 3.5, 45° C. for 60 minutes. In mixtures comprising cellulase and protease (Example 7), the protease is completely inactivated by treating at 3° C. or 25° C. for 60 minutes and at a pH of 2.5.

Some methods described in the art have the disadvantage of being rather laborious. In general the methods in the art are characterised by a low selectivity towards inactivation of amylase and by a relatively high loss in protease activity.

During the microbial production of chymosin and *Rhizomucor miehei* aspartic protease via fermentation, the enzyme amylase is also produced in the fermentation broth. The dairy farming industry is now striving to obtain higher cheese yields and dairy products of superior quality. The latter highly depends upon the purity of the milk-clotting enzymes employed in the production of these products. One of the problems connected with the presence of amylase in milk-clotting enzymes are the unwanted side activities of amylase in the whey, which can be detrimental to further applications of the whey. Therefore one purpose of the invention is to provide a simple and efficient method to inactivate amylase in the presence of *Rhizomucor miehei* aspartic protease with high selectivity and with high recovery of the protease.

Surprisingly it has been found that the inactivation of amylase in the presence of *Rhizomucor miehei* aspartic protease can be achieved by the present invention, which comprises keeping the *Rhizomucor miehei* aspartic protease solution comprising amylase at a pH between 2.1 and 2.8 and at a temperature between 20° C. and 40° C. for a period of time which is sufficient to inactivate amylase for at least 95%. Employing these conditions results in an unexpected increase in amylase deactivation whilst maintaining a high level of aspartic protease activity.

Preferably, the solution is kept at this pH and temperature for a period of time between 0.5 and 24 hours.

Advantages of this method are the simplicity and especially the high selectivity with which amylase is inactivated in *Rhizomucor miehei* aspartic protease solutions comprising amylase. It has been surprisingly found that with the method of the invention at least 90%, preferably at least 95% of aspartic protease activity is maintained in the *Rhizomucor miehei* aspartic protease solution after treatment while the residual amylase activity is generally lower than 0.05 RAU/g, preferably lower than 0.001 RAU/g, more preferably lower than 0.0005 RAU/g.

With the term "amylase" it is intended any enzyme with amylase activity, for example α-amylase (EC 3.2.1.1), β-amylase (EC 3.2.1.2), γ-amylase (EC 3.2.1.3), amylase III (2.4.1.161) or any mixture thereof.

1 RAU (Amylase activity Unit) is defined as the amount of enzyme that will convert under standardized conditions (pH=6.6, 30° C.) 1 mg soluble starch per minute. The IMCU (International Milk Clotting Unit) is defined for bovine rennets by the International Dairy Federation (IDF), protocol 157: 1992.

With the term "*Rhizomucor miehei* aspartic protease" it is intended the aspartic protease homologously produced in *Rhizomucor miehei*. A process for the preparation of the enzyme via fermentation is described in the U.S. Pat. No. 3,988,207. With the term "*Rhizomucor miehei* aspartic protease" it is also intended to encompass a recombinant *Rhizomucor miehei* aspartic protease, i.e. a *Rhizomucor miehei* aspartic protease produced in a host organism transformed with DNA coding for the *Rhizomucor miehei* aspartic protease. The host organism can be a fungus, e.g. a yeast or a filamentous fungus. Preferably the host organism is a filamentous fungus selected from the genera of *Aspergillus, Trichoderma, Penicillium, Fusarium* or *Humicola*. Most preferably, the filamentous fungus belongs to the genera *Aspergillus* or *Trichoderma*. The use of *Aspergillus niger, Aspergillus nidulans* or *Aspergillus oryzae* as a host strain is preferred. Method for the production of a recombinant *Rhizomucor miehei* aspartic protease in a host organism is described in European patent EP0700253B1.

With the term "*Rhizomucor miehei* aspartic protease solution" it is intended a solution, preferably an aqueous solution, comprising amylase and *Rhizomucor miehei* aspartic protease.

The method of the invention can be advantageously applied to *Rhizomucor miehei* aspartic protease derived from fermentation broths or derivatives thereof obtainable at any one of the stages during the down-stream process, generally before the formulation step. The *Rhizomucor miehei* aspartic protease solution is preferably a fermentation broth, most preferably a fermentation broth derived from the fermentation of *Rhizomucor miehei*, which can be obtained according to methods known in the art, for example like described in "Pilot plant experiment" of the U.S. Pat. No. 3,988,207. In another preferred embodiment of the invention, the fermentation broth is a fermentation broth of a host organism transformed with DNA encoding the *Rhizomucor miehei* aspartic protease which organism expresses the protease. Generally, the *Rhizomucor miehei* aspartic protease solution is obtained from the fermentation broth after removal of the cells. The latter may be achieved by killing of the microorganisms in the fermentation broth by one of the several methods known in the art and by removal of the cell debris. Removal of the cells can be achieved by one or more solid/liquid separation techniques like flocculation, centrifugation, filtration, and membrane separation. Generally, the *Rhizomucor miehei* aspartic protease solution is obtained from the fermentation broth after removal of the cells and concentration of the cell free solution prior use in the method of the invention. Concentration may be achieved by evaporation or membrane concentration; preferably the membrane concentration is achieved by ultrafiltration techniques. Therefore in a preferred embodiment of the invention the *Rhizomucor miehei* aspartic protease solution is a cell-free and/or concentrated fermentation broth. With "cell-free" it is intended free of any particle or cell with diameter of 0.4 μm or higher.

It has been observed that the addition of an agent such as sodium chloride to the *Rhizomucor miehei* aspartic protease solution stabilises the *Rhizomucor miehei* aspartic protease decreases the loss in aspartic protease activity during the method of the invention. Examples of these agents are sodium chloride, potassium chloride, glycerol, sorbitol, polyethylene glycol. In a preferred embodiment of the invention, the *Rhizomucor miehei* aspartic protease solution comprises an agent having stabilising effect on *Rhizomucor miehei* aspartic protease. Most preferably the *Rhizomucor miehei* aspartic protease solution comprises sodium chloride. When sodium chloride is present, this is generally added to the fermentation broth in an amount comprised between 50-200 g/kg.

The pH of the *Rhizomucor miehei* aspartic protease solution used in the method of the invention can be adjusted using food acceptable acids or bases well within the knowledge of those skilled in the art. Adjustment of the pH can be effected before during or after the enzyme mixture has reached the heating temperature. However the heating time should start once the solution has the correct pH. In a preferred embodiment of the invention adjustment of the pH of the enzyme mixture is achieved prior to heating the enzyme mixture.

It has been observed that the best results in maintenance of protease activity and inactivation of amylase are obtained when, in a method of the invention, the *Rhizomucor miehei* aspartic protease solution is kept at a pH between 2.3 and 2.6 and/or kept at a temperature between 32° C. and 38° C. Preferably the solution is kept at this pH and temperature for a period of time between 0.5 and 24 hours. Therefore, in a preferred embodiment of the invention the pH of the *Rhizomucor miehei* aspartic protease solution during the inactivation step is between 2.3 and 2.6. In another preferred embodiment the temperature at which the solution is kept during the inactivation step is comprised between 32° C. and 38° C. In a third preferred embodiment the period of time at which the reaction is kept at the desired temperature is between 4 and 12 hours.

Once the amylase inactivation step has been completed, the temperature of the solution is generally decreased to between about 4° C. to 25° C., preferably to 4° C., and the pH of the solution is increased to a value at which the *Rhizomucor miehei* aspartic protease is stable, usually at a pH between about 4 and 6.

With the method of the invention, amylase is inactivated with high selectivity in *Rhizomucor miehei* aspartic protease solutions. At the end of the treatment at least 90%, preferably at least 95% of the aspartic protease activity is maintained while the residual amylase activity is generally lower than 0.05 RAU/g, preferably lower than 0.001 RAU/g, more preferably lower than 0.0005 RAU/g. The level of amylase activity in the *Rhizomucor miehei* aspartic protease solution before the inactivation step is generally 100 RAU/g or higher. Therefore, the degree of amylase inactivation in the solution after the treatment is generally at least 99.95%.

It is known that *Rhizomucor miehei* aspartic protease is highly heat stable. This characteristic can be disadvantageous, as during cheese-making manufacture the enzyme remains partially active in the whey after pasteurisation, causing undesired milk clotting when the whey is used in other preparations. Therefore the *Rhizomucor miehei* aspartic protease comprised in coagulating enzyme preparations is preferably modified to increase its thermal destabilisation. In case the *Rhizomucor miehei* aspartic protease used in a method of the invention has not been treated to increase its thermal destabilisation, the method of the invention can comprise a step, to be applied after the amylase inactivation, to increase the thermal destabilisation of the *Rhizomucor miehei* aspartic protease. The treatment to increase *Rhizomucor miehei* aspartic protease thermal destabilisation can also be applied prior to the amylase inactivation step. In this case the amylase inactivation step is preferably applied at a temperature between 20° C. and 25° C., preferably at about 20° C., the other parameters remaining the same. The enzyme solution preferably comprises sodium chloride or an agent having a stabilising effect on *Rhizomucor miehei* aspartic protease. When sodium chloride is used, this is generally added to the fermentation broth in an amount between 50-200 g/kg.

In a preferred embodiment, after inactivation of amylase the thermal destabilisation of the *Rhizomucor miehei* aspartic protease in the solution is increased with a method known in the art.

The method used to increase the thermal destabilisation of *Rhizomucor miehei* aspartic protease is not critical and may comprise any of the several methods known in the art to perform this task. For example the enzyme product can be treated in an aqueous medium with an oxidising agent containing active halogen, e.g. hypochlorite (e.g. the GB Patent No. 2,045,772B). Another possibility is to treat the enzyme product in aqueous medium with an acylating reagent, e.g. acetic or propionic anhydride (e.g. the GB Patent No. 2,038,339B). Preferably the enzyme product is treated in aqueous medium with a peroxy acid like an inorganic peroxy acid or a lower aliphatic peroxy acid. Preferably peroxy acetic or peroxy propionic acid is used (GB Patent No. 2,045,773). The way to perform these methods is widely described in the literature and therefore well within the knowledge of those skilled in the art.

The invention also provides a *Rhizomucor miehei* aspartic protease obtainable by a method of the invention and further provides compositions comprising such aspartic proteases. The *Rhizomucor miehei* aspartic protease comprises less than 0.0005 RAU amylase per 2000 IMCU protease.

The enzyme product comprising *Rhizomucor miehei* aspartic protease obtainable by a method of the invention can be further processed. Following the amylase inactivation step or the increase in thermal destabilisation of *Rhizomucor miehei* aspartic protease any conventional method known in the art is suitable to prepare the enzyme for further use.

The enzyme product can be used for the preparation of a food stuff. These compositions may comprise other enzymes. Therefore the invention also provides compositions comprising *Rhizomucor miehei* aspartic protease obtainable by a method of the invention. Such compositions may be solid or liquid compositions. The solid compositions may be in the form of tablets, granules, powders, crystals etc.

The *Rhizomucor miehei* aspartic protease obtainable by a method of the invention or alternatively the composition of the invention can be used for the production of a dairy product. Milk of different sources can be used in the production of such product, which preferably is a cheese product. Examples of milk, which are obtainable by the method of the invention, are cow milk, goat milk, sheep milk, camel milk etc. The *Rhizomucor miehei* aspartic protease is suitable for the production of any type of cheese or dairy product. The use of microbial aspartic proteases as clotting enzymes in cheese making is well documented in the art. An advantage of the *Rhizomucor miehei* aspartic protease obtainable by the method of the invention or alternatively the compositions of the invention is the very low level or absence of amylase activity. The use of the enzyme of the invention or of the aforementioned composition as a clotting enzyme in cheese making allows, for example, a more advantageous further processing of the whey obtained after separation of the curd. This whey, being free of amylase activity, can be used with better results for the preparation of dairy products comprising starch, gluten, etc.

The invention will now be illustrated by way of examples, which however should not be considered as limiting.

EXAMPLE 1

The following example shows the results of amylase inactivation in a *Rhizomucor miehei* cell-free, concentrated fermentation broth obtained from a crude *Rhizomucor miehei* fermentation broth after the steps of: 1) solid-liquid separation, 2) polish filtration, and 3) ultrafiltration comprising 100 g/kg of NaCl as stabiliser. The *Rhizomucor miehei* aspartic protease comprised in the fermentation broth has not been treated to increase its thermal destabilisation. The amylase activity and the *Rhizomucor miehei* aspartic protease activity in the solution are measured with standard methods known to those skilled in the art.

TABLE 1

| pH | | | | | 2.5 | | | | | 3.0 | | | |
|---|---|---|---|---|---|---|---|---|---|---|---|---|---|
| Temperature (° C.) | | 20 | | | | 30 | | | | 40 | | | |
| Time (hours) | 2 | 4 | 6 | 8 | 2 | 4 | 8 | 2 | 4 | 6 | 8 | 12 | 24 |
| R. miehei Asp. Protease (%) | 97 | 101 | 100 | 99 | 99 | 102 | 100 | 104 | 97 | 99 | 99 | 102 | 98 |
| Amylase (RAU/g) | 218 | 100 | 30 | 10 | 25 | 5 | 0.01-1 | 150 | 70 | 26 | 6 | <1 | <1 |

TABLE 2

| pH | 2.5 | | | |
|---|---|---|---|---|
| Temperature (° C.) | 35 | | 40 | |
| Time (hours) | 4 | 8 | 4 | 8 |
| R. miehei Asp. prot. (%) | 101 | 100 | 100 | 96 |
| Amylase (RAU/g) | <0.0005 | <0.0005 | <0.0005 | <0.0005 |

Note:
Amylase activities of 1 RAU/g or higher are measured via UV-Vis absorption. Activities lower than 1 RAU/g are measured via a Petri dish method. The detection limit is 0.0005 RAU/g.

Table 1 shows the residual amylase and the residual aspartic protease activity after treatment, the latter effected at a pH between 2.5 and 3.0, a temperature between 20° C. and 40° C., for a time between 2 and 24 hours, on a cell-free, concentrated fermentation broth comprising 3950 IMCU/g R. miehei aspartic protease activity and 520 RAU/g amylase activity Table 2 shows the same values at a pH of 2.5, a temperature between 30° C. and 40° C., for a time between 4 and 8 hours, on a cell-free, concentrated fermentation broth comprising 2000 IMCU/g R. miehei aspartic protease activity and 250 RAU/g amylase activity.

These experiments show that to obtain optimal amylase inactivation (i.e. at least 99.99% amylase inactivation) in *Rhizomucor miehei*, cell-free, concentrated fermentation broth comprising *Rhizomucor miehei* aspartic protease which has not been treated to increase its thermal destabilisation, with minimal losses in aspartic protease activity, the following conditions can be applied: a pH of about 2.5, a temperature of about 35° C. and a heating time of about 4 hours.

EXAMPLE 2

This example shows the results of amylase inactivation treatment effected on *Rhizomucor miehei* cell-free, concentrated fermentation broth prestabilised with 100 g/kg of NaCl.

TABLE 3

| | Batch | | | | | |
|---|---|---|---|---|---|---|
| | 1 | | 2 | | 3 | |
| Time (h) | Amylase (RAU/g) | R. miehei Asp. Prot. (%) | Amylase (RAU/g) | R. miehei Asp. Prot. (%) | Amylase (RAU/g) | R. miehei Asp. Prot. (%) |
| 0 | 225 | 100 | 490 | 100 | 550 | 100 |
| 4 | <0.0005 | 101 | 0.001-0.005 | 98 | Nd | Nd |
| 5 | Nd | Nd | 0.0005-0.001 | 98 | Nd | Nd |
| 6 | Nd | Nd | <0.0005 | 96 | 0.0005 | 98 |
| 8 | <0.0005 | 100 | Nd | Nd | Nd | Nd |

Note:
Amylase activities of 1 RAU/g or higher are measured via UV-Vis absorption. Activities lower than 1 are measured via a Petri dish method. The detection limit is 0.0005 RAU/g.
Nd = not determined.

Table 3 shows the residual amylase and the residual aspartic protease activity after treatment effected at pH 2.5, a temperature of 35° C. for between 0 and 8 hours. Batch 1 comprises 2000 IMCU/g R. miehei aspartic protease, 250 RAU/g amylase, batch 2 comprises 3990 IMCU/g R. miehei aspartic protease, 626 RAU/g amylase and batch 3 comprises 3389 IMCU/g R. miehei aspartic protease, 701 RAU/g amylase.

These results show that inactivation of amylase in *Rhizomucor miehei* cell-free, concentrated fermentation broth derivatives comprising sodium chloride and *Rhizomucor miehei* aspartic protease which has not been treated to increase its thermal destabilisation, can be achieved within 4 hours with average aspartic protease activity losses lower than 5%.

EXAMPLE 3

The following example shows the results of amylase inactivation in *Rhizomucor miehei* cell-free, concentrated fermentation broths comprising *Rhizomucor miehei* aspartic protease, which has been treated to increase its thermal destabilisation. The concentrates have been stabilised with 100 g/kg of sodium chloride. The results of the experiments, expressed as residual amylase activity and residual *Rhizomucor miehei* aspartic protease activity after the inactivation step are shown in Table 4. All experiments have been executed at 20° C., at a pH between 2.3 and 2.7, for a time of 0 to 8 hours.

TABLE 4

| Time | Assay 1 pH 2.5 | | Assay 2 pH 2.3 | | Assay 3 pH 2.7 | |
|---|---|---|---|---|---|---|
| (h) | Amyl | RAF | Amyl | RAF | Amyl | RAF |
| 0 | 125 | 100 | 125 | 100 | 125 | 100 |
| 6 | 0.018 | 97 | 0.013 | 95 | 0.029 | 96 |
| 8 | 0.018 | 99 | 0.013 | 94 | 0.027 | 99 |

Note:
Amyl: residual amylase activity (RAU/g);
RAF: percentage of residual *Rhizomucor miehei* aspartic protease activity.
Amylase activities of 1 RAU/g or higher are measured via UV-Vis absorption. Activities lower than 1 are measured via a Petri dish method. The detection limit is 0.0005 RAU/g.

These results show that with *Rhizomucor miehei* solutions comprising *Rhizomucor miehei* aspartic protease, which has been treated to increase its thermal stabilisation, higher aspartic protease activity losses and higher levels of residual amylase activity can be observed. However the losses in protease activity are always lower than 10%, and the residual amylase activity is always lower than 0.05 RAU/g (i.e. the degree of amylase inactivation is 99.98%).

The invention claimed is:

1. A method to inactivate amylase in a solution containing an aspartic protease from *Rhizomucor miehei* and said amylase, which method comprises incubating said solution at a pH between 2.1 and 2.8 and at a temperature between 20° C. and 40° C. for a period of time sufficient to inactivate at least 95% of amylase activity; wherein residual protease activity in the solution at the end of the incubation is at least 90% of protease activity at the beginning of the incubation.

2. The method of claim 1, wherein said time is between 0.5 and 24 hours.

3. The method of claim 1, wherein residual amylase activity is 0.05 RAU/g or lower.

4. The method of claim 1, wherein the pH is between 2.3 and 2.6.

5. The method of claim 1, wherein the temperature is between 32° C. and 38° C.

6. The method of claim 2, wherein said time is between 4 and 12 hours.

7. The method of claim 1, wherein the solution is a cell-free and/or concentrated fermentation broth.

8. The method of claim 7, wherein the fermentation broth is from a filamentous fungus selected from the group consisting of *Aspergillus*, *Trichoderma*, *Penicillium*, *Fusarium*, and *Humicola*.

9. The method of claim 1, which further comprises increasing thermal destabilisation of the aspartic protease.

10. The method of claim 1, which further comprises increasing thermal destabilisation of the aspartic protease prior to said incubation step.

11. The method of claim 10, wherein said inactivating step is carried out at a temperature between 20° C. and 25° C.

12. A protease composition comprising an aspartic protease from *Rhizomucor miehei*, wherein said composition comprises less than 0.001 RAU of amylase per 2000 IMCU of protease.

13. A second composition comprising the protease composition of claim 12.

14. The second composition of claim 13, which is a solid or a liquid composition.

15. The second composition of claim 14, which is in the form of a tablet, a powder or a granule.

16. A method to produce a dairy product which method comprises coagulating a dairy product preparation by contacting said preparation with the protease composition of claim 12 or a second composition thereof.

17. The method of claim 16, wherein the dairy product is a cheese product.

18. The composition which is obtainable by the method of claim 1.

19. A method to inactivate amylase in a solution containing (i) an aspartic protease from *Rhizomucor miehei*, (ii) a stabilizing agent for the aspartic protease, and (iii) said amylase, which method comprises incubating said solution at a pH between 2.1 and 2.8 and at a temperature between 20° C. and 40° C. for a period of time sufficient to inactivate at least 95% of amylase activity; wherein residual protease activity in the solution at the end of the incubation is at least 90% of protease activity at the beginning of the incubation.

20. The method of claim 19, wherein said time is between 0.5 and 24 hours.

21. The method of claim 20, wherein said time is between 4 and 12 hours.

22. The method of claim 19, wherein residual amylase activity is 0.05 RAU/g or lower.

23. The method of claim 19, wherein the pH is between 2.3 and 2.6.

24. The method of claim 19, wherein the temperature is between 32° C. and 38° C.

25. The method of claim 19, wherein the solution is a cell-free and/or concentrated fermentation broth.

26. The method of claim 25, wherein the fermentation broth is from a filamentous fungus selected from the group consisting of *Aspergillus, Trichoderma, Penicillium, Fusarium,* and *Humicola*.

27. The method of claim 19, wherein the stabilising agent is sodium chloride.

28. The method of claim 19, which further comprises increasing thermal destabilisation of the aspartic protease.

29. The method of claim 19, which further comprises increasing thermal destabilisation of the aspartic protease prior to said incubation step.

30. The method of claim 29, wherein said inactivating step is carried out at a temperature between 20° C. and 25° C.

31. A protease composition comprising an aspartic protease from *Rhizomucor miehei* and a stabilising agent for the aspartic protease, wherein said composition comprises less than 0.001 RAU of amylase per 2000 IMCU of protease.

32. A second composition comprising the protease composition of claim 31.

33. The second composition of claim 32, which is a solid or a liquid composition.

34. The second composition of claim 33, which is in the form of a tablet, a powder or a granule.

35. The composition of claim 31, wherein the stabilising agent is sodium chloride.

36. The composition which is obtainable by the method of claim 19.

37. A method to produce a dairy product which method comprises coagulating a dairy product preparation by contacting said preparation with the protease composition of claim 31 or a second composition thereof.

38. The method of claim 37, wherein the dairy product is a cheese product.

\* \* \* \* \*